US00PP36674P3

(12) United States Plant Patent
Hansen

(10) Patent No.: US PP36,674 P3
(45) Date of Patent: May 13, 2025

(54) ***ARUNCUS* PLANT NAMED 'Goatee'**

(50) Latin Name: ***Aruncus* hybrid**
Varietal Denomination: Goatee

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 176 days.

(21) Appl. No.: 18/445,326

(22) Filed: Jul. 11, 2023

(65) Prior Publication Data

US 2025/0024764 P1 Jan. 16, 2025

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05); *A01H 5/02* (2013.01)

(58) Field of Classification Search
USPC ..... Plt./263.1
CPC ..... A01H 5/02
See application file for complete search history.

*Primary Examiner* — Kent L Bell

(57) ABSTRACT

The new hybrid *Aruncus* plant named 'Goatee' with sharply-lobed, dentate, tri-pinnately compound, dark-green foliage holding well into the season. Light creamy buds transition to near-white flowers on airy scapes, above foliage on heavily branched panicles with nearly horizontal branches.

2 Drawing Sheets

Botanical denomination: *Aruncus* hybrid.
Cultivar designation: 'Goatee'.

STATEMENT REGARDING PRIOR DISCLOSURES UNDER 37 CFR 1.77(B)(6)

The first non-enabling disclosure of the claimed plant was Feb. 1, 2023, when the claimed plant was displayed as a photograph with a non-enabling brief description on a website maintained by Walters Gardens, Inc. This was followed by the "Walters Gardens 2023-2024 Catalog" first sent out on May 19, 2023. The first offer for sale of *Aruncus* 'Goatee' was by Walters Gardens, Inc. on Jul. 28, 2022. Walters Gardens, Inc. obtained the new plant and all information about the new plant directly from the inventor. No plants have been sold earlier than this date anywhere in the world, nor has any disclosure, or offer for sale, of the new plant been made more than one year prior to the filing date of this application, and such disclosure within one year was either derived directly or indirectly from the inventor.

BACKGROUND OF THE INVENTION

The present invention relates to a new and distinct plant of Goat's Beard. The new plant was first selected from initial evaluations by the inventor at a wholesale perennial nursery in Zeeland, Michigan, USA in the spring of 2017 from seedlings that were sown in the spring of 2016. The single seedling selected as the new plant was from a batch of seed resulting from a self-pollination of 'Fairy Hair' U.S. Plant Pat. No. 30,242 on Jun. 8, 2015. The new plant was selected from among many other seedlings growing at the same nursery in Zeeland, Michigan which met the rigorous criteria of excellent foliage and habit established as breeding goals. 'Goatee' has been asexually propagated since 2019 by shoot tip tissue culture at the same nursery in Zeeland, Michigan. The resultant asexually propagated plants have remained stable and exhibit the identical characteristics as the original plant in multiple generations.

BRIEF SUMMARY OF THE INVENTION

'Goatee' differs from all other Goat's Beard known to the applicant. Compared with the parent the habit of 'Goatee' is taller, the foliage is less dissected, and the flower panicles are denser.

The nearest known cultivar to 'Goatee' is 'Chantilly Lace' U.S. Plant Pat. No. 30,740. Other comparable plants include 'Misty Lace' U.S. Plant Pat. No. 15,798.

'Misty Lace' is taller and narrower in habit. 'Chantilly Lace' is slightly larger and broader in habit with finer leaf texture and finer raceme texture. 'Goatee' flowers slightly later with more dense panicles than either of the above comparison cultivars.

The new plant, 'Goatee', differs from all *Aruncus* known to the inventor in the following combined traits:

1. The foliage is tri-pinnately compound, dentate, sharply-lobed, and dark-green colored.
2. Flowers are near-white on airy scapes above the plant.
3. Panicle branches are nearly horizontal.
4. Plant habit is medium height and width.

BRIEF DESCRIPTION OF THE DRAWINGS

The photographs of the new plant demonstrate the overall appearance of 'Goatee' including the unique traits. The plant in the photographs is of a three-year-old plant grown in a full-sun trial garden at a wholesale perennial nursery in Zeeland, Michigan, USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
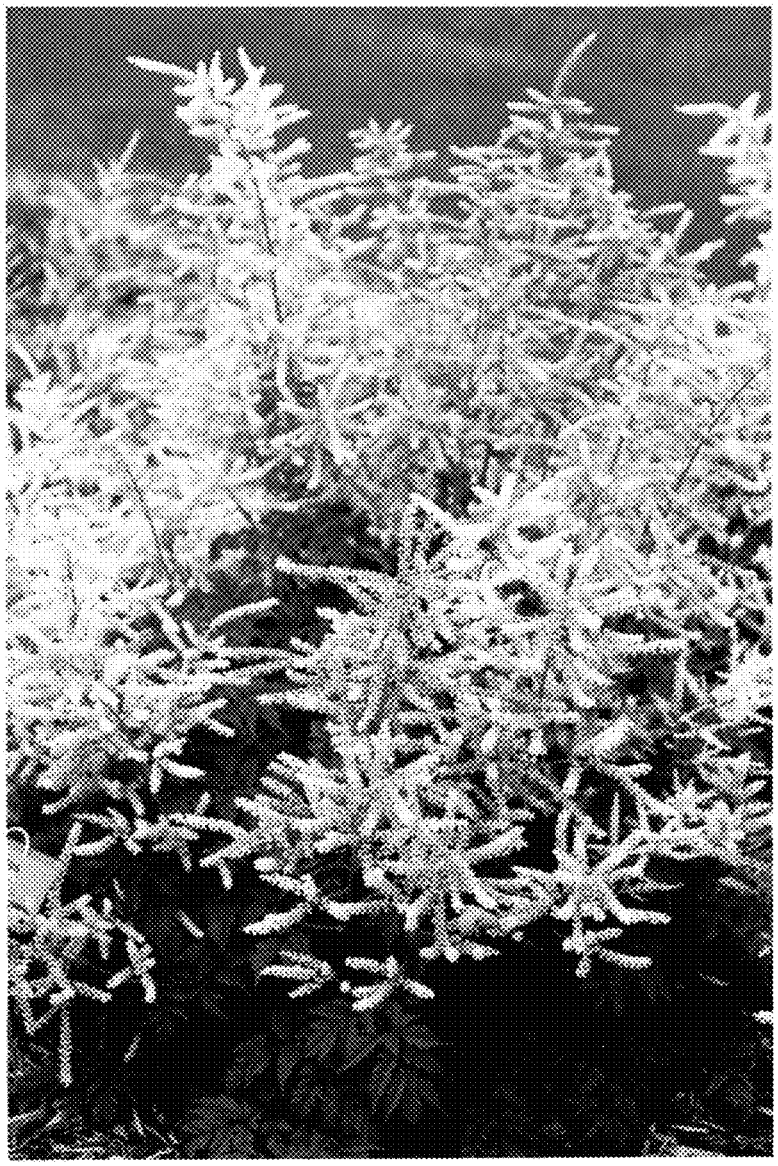
FIG. 1 shows the habit of late spring flowering together with the tripinnately compound leaves.
Figure 2:
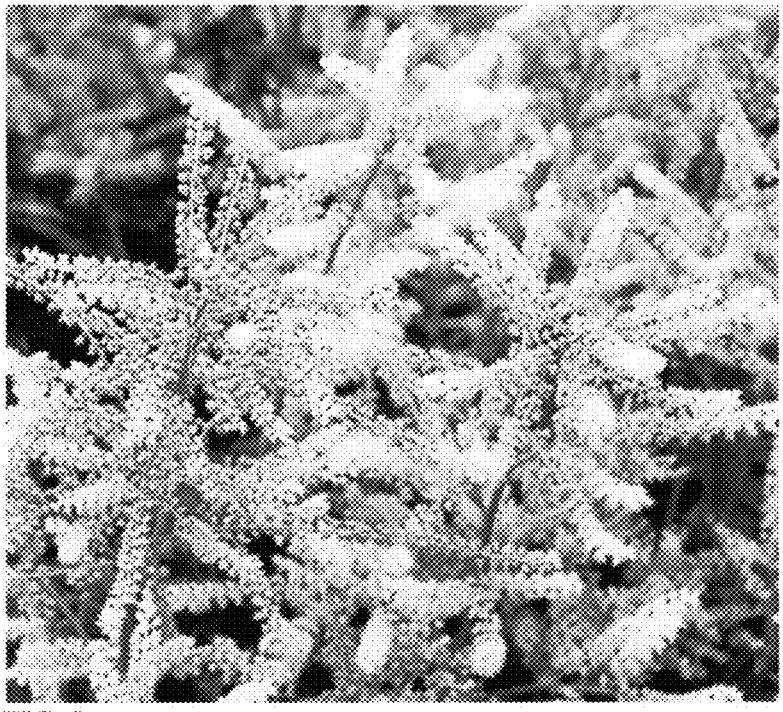
FIG. 2 shows a close-up of the panicles with flowers and buds.

The following description is based on two-year-old plants growing in a double poly greenhouse with supplemental water and fertilizer at a wholesale perennial nursery in Zeeland, Michigan, USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The parent is 'Fairy Hair';

Plant habit: Hardy herbaceous perennial of dense short stems producing compact mounded habit; foliage about 30 cm tall and 38 cm across; flowering to about 54 cm tall;

Roots: Fibrous, finely branched; cream to light tan in color depending on soil type;

Growth rate: Moderate, from tissue culture liner to finishing in a three-liter container in about 3 months; beginning to flower in 7 to 9 weeks following a 9-week vernalization period;

Stems: Cylindrical; glabrous; slightly lustrous; about 6 per plant; flowering stems to about 44 cm tall and 7 mm diameter at base;

Stem color: Nearest RHS 146D with a slight overtone in the middle portion of nearest RHS 180B in regions of high light exposure;

Internode: Variable from 20 mm near the middle to 4 mm proximally average about 15 mm; about 34 per stem;

Internode color: Between RHS 146D with undertones of RHS 180B in regions with more light intensity;

Foliage: Blade or lamina glabrous abaxial and adaxial; tri-pinnately dissected; typically with five pinna;

Pinna: Basal pinna to 6 cm long and 6 cm wide with basal pinnule to 4.0 cm long and 3.5 mm wide, apical pinnule to about 5.2 cm long and 5.0 cm wide; decreasing in pinna pinnule distally; pinna attached with concavo-convex, glabrous rachilla to about 18 mm long and 1 mm across; separated on rachis to about 4.5 cm, decreasing distally;

Pinnule: Ovate; apex narrowly acute; base abruptly cuneate; five-lobed and individual lobes dissected and dentate with at least five lobes to about 11 mm long and 3.5 mm across at base, teeth about 1 to 2 mm long and 1 mm across; attached with pinnula rachilla; pinnule attached with rachilla to about 4 mm long and 0.5 mm across;

Rachis: Glabrous; concavo-convex; upright to outwardly; to about 8 cm long and 2 mm wide above proximal pinna;

Pinna rachis: Glabrous; slightly concavo-convex; to about 18 mm long and about 1 mm wide on proximal pinnule and about 10 mm long and 0.7 mm wide on distal pinnule;

Pinnule rachilla: Glabrous; slightly concavo-convex; to about 6 mm long and 0.5 mm across;

Rachis and rachilla color: Adaxial between RHS 145A and RHS 146D, abaxial between RHS 145D and RHS 146D;

Petiole: Concavo-convex distally to horizontally applanate proximally; glabrous; swollen at base; to about 7.5 cm long, 8 mm across at base, and about 3 mm across below pinna; average about 5.8 cm long, 4 mm across at base, and 2 mm across below pinna;

Petiole color: Variable, adaxial between RHS 146D and RHS 145A with moderate blush of nearest RHS 180B to nearly solid RHS 180B; abaxial between RHS 160C and RHS 162C with faint to moderate blush of nearest RHS 180B;

Foliage color: Leaf color is seasonally variable; young expanding leaves adaxial and abaxial surfaces nearest RHS 146A; mid-season to fall adaxial nearest RHS NN137B and abaxial nearest RHS 137B;

Leaf surface: Glabrous, dull, and matte adaxial and abaxial;

Leaf quantity: Dense, diameter with up to 14 leaves per stem;

Veins: Pinnate; glabrous adaxial and abaxial;

Vein color: Adaxial nearest RHS 145B and abaxial between RHS 145C and RHS 150C;

Inflorescence: In alternate, loosely-branched, airy panicle; about 6 panicles per plant with about 600 flowers per panicle; first panicle flowering beginning in late spring; individual panicles remaining in flower for about three weeks; flower attitude mostly outwards; individual flowers remaining effective for about 4 days;

Fragrance: None detected;

Peduncle: Panicle; terete; erect; glabrous; to about 54 cm tall and 7 mm diameter at base; flowering portion about 38 cm long and 15 cm across;

Peduncle attitude: Main panicle upright, panicle branchlets slightly drooping;

Peduncle branches: To about 32 per stem; ascending to about 45 degrees above horizontal; terete; glabrous; to about 20 cm long and 1.0 mm diameter; branchlets compound, to about 6 cm long and 1.5 cm wide; with flowers non-secund;

Peduncle color: Nearest RHS 146C distally and ventrally, and nearest RHS 146D with moderate overtone of nearest RHS 180B dorsally and where exposed to high light;

Pedicel: Terete; glabrous; to about 1.5 mm long and 0.2 mm in diameter;

Pedicel color: Between RHS 145C and RHS 146D;

Buds one day prior to opening: Globose to ellipsoidal; with rounded apex, and rounded base; about 2 mm long and 1.5 mm diameter;

Bud color: Exposed petals between RHS NN155B and RHS NN155A;

Flower: Campanulate, actinomorphic; individual flowers lasting about four days on plant or as cut panicle;

Flower size: To 5 mm wide and 3 mm deep to exserted stamens, corolla to about 4 mm across and 2 mm deep;

Calyx: Campanulate; comprising five sepals;

Sepals: Five; lanceolate to deltoid; acute apex; truncate base; glabrous abaxial and adaxial; about 0.7 mm long and 0.3 mm wide at base;

Sepal color: Abaxial and adaxial distally nearest RHS 183A and proximally nearest a blend between RHS 179D and RHS 161D;

Petals: Five; obelliptic; rounded apex; attenuate base; margin entire; glabrous adaxial and abaxial; about 1.5 mm long and 0.7 mm wide;

Petal color: Adaxial and abaxial nearest RHS NN155B;

Androecium: About 25;

*Filaments.*—Variable lengths from 1 mm to 3 mm long and about 0.1 mm diameter; color nearest RHS NN155D.

*Anthers.*—Globose; about 0.3 mm diameter; color nearest RHS NN155B.

*Pollen.*—Abundant; color nearest RHS NN155B.

Gynoecium: Single; about 1.5 mm long;

*Ovary.*—Superior; about 0.5 mm diameter; color between RHS 155C and RHS NN155C.

*Style.*—About 0.5 mm long and 0.2 mm diameter; color between RHS 155C and RHS NN155C.

*Stigma.*—Acute; about 0.1 mm across; color between RHS 155C and RHS NN155C.

Fruit: Typically, with three seeds per fruit, rarely four;

Seed: Caudate; to about 3 mm long and less than 1 mm wide; color nearest RHS 146C as developing, mature between RHS 166A and RHS 166B;

Growth: *Aruncus* 'Goatee' grows best with ample moisture and good drainage in part shade or protection from sun in the hottest part of the day. Cold hardy from USDA zones 3 to 7.

Disease and pest tolerance: Pest and disease resistance and tolerance outside of that normal for *Aruncus* is not known at this time.

It is claimed:

1. A new and distinct ornamental plant named *Aruncus* 'Goatee' as herein described and illustrated.

* * * * *